United States Patent [19]
Stiekema et al.

[11] Patent Number: 5,932,784
[45] Date of Patent: Aug. 3, 1999

[54] METHOD FOR OBTAINING MALE-STERILE PLANTS

[75] Inventors: Willem Johannes Stiekema, Wageningen; Andy Pereira, Ede; Mark Gerardus Maria Aarts, Bennekom, all of Netherlands

[73] Assignee: Centrum Voor Plantenveredelings en Reproduktieonderzoek (CPRO-DLO), Wageningen, Netherlands

[21] Appl. No.: 08/545,745

[22] PCT Filed: May 3, 1994

[86] PCT No.: PCT/NL94/00096

§ 371 Date: Jan. 11, 1996

§ 102(e) Date: Jan. 11, 1996

[87] PCT Pub. No.: WO94/25593

PCT Pub. Date: Nov. 10, 1994

[30] Foreign Application Priority Data

May 3, 1993 [EP] European Pat. Off. .............. 93201233

[51] Int. Cl.⁶ .............................. A01H 5/00; A01H 1/02; C12N 15/29; C12N 15/82
[52] U.S. Cl. ......................... 800/303; 800/274; 800/278; 800/286; 800/287; 800/298; 435/419; 435/468; 536/23.6; 536/24.1; 536/24.5
[58] Field of Search .................................. 536/23.6, 24.1, 536/24.5; 435/172.3, 419, 468; 800/205, 250, 274, 278, 286, 287, 298, 303; 47/58, DIG. 1

[56] References Cited

FOREIGN PATENT DOCUMENTS

| 0329308 | 8/1989  | European Pat. Off. . |
| 0513884 | 11/1992 | European Pat. Off. . |
| 9011682 | of 0000 | WIPO . |
| 9008828 | 8/1990  | WIPO . |
| 9211379 | 7/1992  | WIPO . |
| 9302197 | 2/1993  | WIPO . |

OTHER PUBLICATIONS

Aarts, M.G.M., et al. 'Transposon Tagging of a Male . . . ' Nature, vol. 363, Jun. 24, 1993, London GB, pp. 715–717.
Wilson, Z.A., et al. 'Chromosome Walking as an Approach . . . ' J. Exp. Bot., vol. 42, No. 238, 1991, Suppl., p. 35 (Abstract Only).
Baker, B. et al. "Phenotypic Assay for Excision . . . " vol. 6,1 The EMBO Journal, IRL Press Limited, Oxford, England pp. 1547–1.
Bevan M. "Binary Agrobacterium . . . " Nucleic Acids Research, vol. 12, No. 22, (1984) Oxford University Press pp. 8711–8712.
Crossway, A. et al., "Integration of Foreign . . . " Mol Gen Genet (1986) 202 179–187.
Dellaporta S.L. et al. "A Plant DNA . . . " pp. 19–21 Plant Molecular Biology Reporter vol. 1, No. 4, Fall 1983.
Detrez, G et al "Phenotypic and Karyotypic . . . " Theor Appl. Genet (1989) 77: 462–468.
Devereux, J. et al. "A Comprehensive Set of Sequence . . . " Nucleic Acids Research 12(1): 387–395 (1984).
Frey, M. et al. "The Maize En–1/spm Element . . . " Mol Gen Genet (1989) 217 (Springer–Verlag Berlin, Germany) pp. 172–1.
Hedin, P. et al "Roles of Flavenoids . . . " Plant Flavenoids in Biology and Medicine: Biochemical, Pharmacological and Structure–Activity Relationship (1986). pp. 87–100, Alan R. Liss, Inc.
Horsch, R.B. et al. "A Simple and General . . . " Science (1985) vol. 277, American Association for the Advancement of Science, Washington, USA. pp. 1229–1231.
Jacobs, M. et al. "Naturally Occurring Anxin . . . " Science (1985) vol. 241, A.R. Liss Inc. pp. 346–349.
Kaulen, H. et al. "Light–Induced Expression . . . " 1986 EMBO Journal, vol. 5, Oxford University Press England pp. 1–8.
Klein, T.M. "High–Velocity Microprojectiles . . . " Nature, vol. 327, (1987) Maxmillan Magazines Ltd. London pp. 70–73.
Koncz, C. et al., "The Promoter of tl–DNA . . . " Mol Gen Genet, (1986) vol. 204, pp. 384, 388/389 Berlin, Gem Springer Verlag.
Krens, F.A. et al "In vitro Transformation . . . " Nature (1982) vol. 296, Macmillan Journals Ltd. London UK pp. 72–7.
Lamb, C.T. et al, "Signals and Transduction . . . " Cell, vol. 56, 215–224, Jan. 27, 1989 pp. 215–224.
Long, S.R. "RhizoGium–Legame, Nodulation . . . " Cell, vol. 56, pp. 203–214 Jan. 27, 1989, Cambridge, Mass US.
Masson, P. "Mobility of the Maize . . . " Proc. Nat'l Acad. Sci (1989) vol. 86, pp. 2219–2223.
McClintock, B. "Mutations in Maize . . . " Carnegie Inst. Washington Year Book, (1954) pp. 254–260 U.S.A.
Negrutiu, I. "Direct Genene Transfer . . . " Plant Physiol. Biochem., 1987, 25(4) pp. 493–503.
Ochman, H. et al., "Genetic Applications . . . " Genetics, (1988) vol. 120, pp. 621–623 Genetics Soc. of America.
Murashize T. et al. "A Revised Medium . . . " Physiology Plantarum, vol. 15, 1962 pp. 473–497.
Pereira, A. et al. "Molecular Analysis . . . " EMBO Journal, vol. 5, No. 5 pp. 835–841, 1986.
Pereira, A. et al. "Transpositional Behavior . . . " EMBO Journal, vol. 8, No. 5. pp. 1315–1321, 1989.
Peterson, P.A. "A Metable Pale Green Locus . . . ". Genetics, (1953) vol. 38, pp. 682–683 (Genetic Soc. of America USA.

(List continued on next page.)

*Primary Examiner*—David T. Fox
*Attorney, Agent, or Firm*—Ladas & Parry

[57] ABSTRACT

A recombinant polynucleotide which can be used for obtaining a male-sterile plant comprising an inhibitor gene capable of inhibiting the expression of a target gene encoding MS2 protein or a homologous target gene and a promoter that is active in the tapetum. A method for obtaining male-sterile plants. Cells, fruit, seeds and progeny of male-sterile plants are also described.

13 Claims, 10 Drawing Sheets

OTHER PUBLICATIONS

Pietrzak, M. et al. "Expression in Plants . . ." Nucleic Acids Research (1986) vol. 14, No. 14 pp. 5857–5868.

Schwarz–Sommer, Z et al. "Sequence Comparison of States . . ." EMBO Journal vol. 4, No. 10. pp. 2439–244 (198.

Schmelzer, E. "In situ Localization . . ." Proc. Natl. Acad. Sci. USA vol. 85, pp 2989–2993 Botany.

Shillito, R.D. et al. "High Efficiency Direct . . ." Bio/Technology, (1985.) vol. 3, pp. 1099–1103 Macmillan London U.

Spencer, D.F. et al. "Sequence and Organization . . ." Plant Molecular Biology, (1992) vol. 20, pp. 347–352 Kluwer Academic Publishers, Dordrecht, Netherlands.

Valvekens, D. et al. "Agrobacterium Tumefaciens . . ." Proc. Natl. Acad. Sci. USA vol. 85, pp. 5536 5540 Aug. 1988, Botany.

Van Den Elzen et al "A Chlmaeric Hygromicin . . ." Plant Molecular Biology (1985) vol. 5, pp. 299–302.

Von der Veen et al. "EMS–Induced Genic Male . . ." Euphytica 17(1968). 371–377 Netherlands.

Weigel, D. "LEAFY Controls . . ." Cell, vol. 69, 843–849 (May 29, 1992) Cell Press.

Wing, D. Et al. "Conserved Function . . ." Mol. Gen. Genet (1989) 219:9–16 pp. 10–11.

Meyer, "Homology–Dependent Gene Silencing in Plants", Annu Rev. Plant Physiol. Plant Mol. Bio., 1996, 47:23–48.

Aarts et al. Plant J 12(3): 615–623 1997.

Lewin, R. 1987. Science 237: 1570.

Reeck et al. 1987. Cell 50: 667.

Napoli et al. 1990. Plant Cell 2: 279–289.

Smith et al. 1988. Nature 334: 724–726.

|     |     |     |     |     |     |     |     |     |     |     |     |     |     |     |     |     |     |     |     |       |
| --- | --- | --- | --- | --- | --- | --- | --- | --- | --- | --- | --- | --- | --- | --- | --- | --- | --- | --- | --- | ----- |
|     |     |     |     |     |     |     |     |     |     |     |     |     |     |     |     |     |     |     |     | -61   |
| GGT | TTA | CTT | AAT | CTT | CTT | TCT | AGT | TAA | GTA | TAT | TCT | TGT | TGC | TCA | TCA | -AT | TCT | GTT | CTT | -1    |
| Met | Glu | Ala | Phe | Leu | Ser | Ser | Ser | Ser | Val | Thr | Ile | Ser | Val | Gly | Ser | Asn | Lys | Leu | Thr | 20    |
| ATG | GAG | GCT | TTC | TTG | AGT | TCT | TCT | TCC | GTA | ACA | ATT | TCC | GTG | GGG | TCA | AAC | AAG | CTT | ACT | 60    |
| Arg | Leu | His | Asn | His | Cys | Val | Trp | Ser | Thr | Val | Ile | Arg | Asp | Gly | Lys | Lys | Arg | Phe | Gly | Pro   |
| AGG | TTA | CAC | AAC | CAT | TGT | GTC | TGG | TCT | ACA | GTG | ATT | AGA | GAT | GGG | AAA | AAG | AGG | TTC | GGT | CCC 120 |
| Thr | Trp | Cys | Arg | Val | Gly | Gly | Gly | Gly | Thr | Val | Gly | Arg | Asp | Asn | Ser | Asn | Arg | Glu | Ala | Ser 60 |
| ACT | TGG | TGC | CGT | GTA | GGT | GGT | GGT | GGT | ACA | GTG | GGG | AGA | GAT | AAC | AGT | AAC | AGG | GAA | GCA | AGT 180 |
| Ile | Arg | Ser | Val | Ser | Leu | Leu | Lys | Asp | Arg | Gly | Leu | Ser | Ile | Gly | Asn | Ile | Arg | Glu | Gln | Ser 80 |
| ATT | CGG | TCT | GTT | TCG | CTT | TTG | AAA | GAC | AGA | GGT | GTA | CTG | ATT | GGG | AAT | AGG | AGA | GAA | CAG | AGT 240 |
| Pro | Ala | Met | Asp | Ala | Glu | Thr | Leu | Val | Leu | Val | Gln | Pro | Asn | Gly | Ser | Met | Val | Gly | Thr | Ile Glu |
| CCG | GCT | ATG | GAT | GCT | GAG | ACA | TTG | GTT | CTG | GTA | CAG | CCA | AAC | GGG | TCT | ATG | GTG | GGG | ACC | ATT GAG 100 300 |
| Ile | Asn | Gly | Val | Lys | Ile | Thr | Leu | Met | Pro | Gly | Ala | Ser | Lys | Phe | Ala | Ile | Thr | Met | Gly | Lys Glu 120 |
| ATC | AAT | GGA | GTA | AAG | ATA | ACT | TTG | ATG | CCT | GGC | GCT | TCT | AAG | TTT | GCT | ATC | ACT | ATG | GGG | AAA GAA 360 |
| Gly | Leu | Gly | Gly | Ile | Ser | Phe | Gln | Gly | Lys | Lys | Phe | Ile | Leu | Leu | Phe | Ile | Gly | Ser | Thr | Gly 140 |
| GGA | CTT | GGC | GGT | ATC | AGT | TTC | CAA | GGG | AAG | AAG | TTT | ATC | CTA | CTG | TTT | ATC | GGC | TCG | ACC | GGT 420 |
| Phe | Leu | Ala | Lys | Val | Leu | Ile | Glu | Lys | Val | Leu | Arg | Met | Ala | Pro | Arg | Met | Pro | Asp | Val | Ser Lys Ile |
| TTC | TTA | GCT | AAA | GTA | CTG | ATT | GAG | AAA | GTC | TTG | AGA | ATG | GCT | CCT | AGA | ATG | CCT | GAT | GTC | AGC AAG ATA 160 480 |

| | | | | | | | | | | |
|---|---|---|---|---|---|---|---|---|---|---|
| Tyr TAT | Leu CTC | Leu TTG | Ile AAT | Lys AAA | Ala GCC | Lys AAA | Ser AGC | Glu GAA | Ala GCT | Ile ATC | Leu CTA | Lys AAG | Asn AAC | Glu GAG | Val GTG | 180 540 |
| Leu TTA | Asp GAT | Ala GCA | Glu GAG | Leu CTT | Phe TTT | Asn AAT | Thr ACT | Leu CTA | Glu GAG | Ala GCT | His CAT | Thr ACT | Tyr TAC | Met ATG | Ser TCT | Phe TTC | 200 600 |
| Met ATG | Leu TTA | Thr ACT | Lys AAA | Leu CTC | Phe TTT | Ile ATC | Pro CCT | Val GTG | Thr ACC | Gly GGA | Asn AAC | Ile ATT | Cys TGC | Asp GAT | Ile GGG | Leu TTG | Gln CAA | 220 660 |
| Ala GCA | Asp GAT | Ser TCA | Ala GCT | Glu GAA | Glu GAG | Ile ATT | Ala GCG | Ala GCA | Lys AAA | Glu GAA | Val GTT | Asp GAT | Ile ATA | Ser TCT | Ala GCT | Ala GCT | Asn AAT | 240 720 |
| Thr ACA | Phe TTC | Asn AAT | Glu GAA | Arg AGA | Tyr TAC | Asp GAT | Cys TGC | Lys AAG | Val GTT | Asp GAT | Ile ATC | Asn AAC | Ile ATA | Arg AGA | Ser TCT | Pro CCC | Gly GGT | Asn AAT | 260 780 |
| Leu CTC | Met ATG | Gly GGA | Phe TTC | Ala GCA | Lys AAG | Cys TGC | Lys AAG | Leu CTG | Lys AAA | Asp GAC | Leu CTG | Ile ATC | Ile ACA | Arg AGA | Gln CAA | Val GTA | Ser TCC | Thr ACA | Ala GCT | 280 840 |
| Tyr TAT | Val GTG | Asn AAT | Gly GGA | Gln CAA | Arg AGA | Gly GGA | Arg AGG | Ile ATC | Met ATG | Glu GAG | Lys AAG | Leu CTG | Phe TTT | Ser TCT | Met ATG | Gly GGA | Asp GAT | Glu GAG | Met ATG | 300 900 |
| Ile ATA | Ala GCA | Thr ACA | Glu GAG | Asn AAC | Phe TTC | Ala GCT | Gln CAA | Arg AGA | Leu CTC | Glu GAA | Asn AAC | Agr AGA | Lys AAA | Ala GCA | Leu TTA | Val GTT | Asp GAT | Arg AGA | Glu GAG | 320 960 |
| Lys AAG | Leu TTA | Ala GCA | Leu CTT | Glu GAA | Ala GCT | Ala GCT | Arg AGA | Lys AAA | Gly GGG | Thr ACT | Gln CAA | Asn AAT | Gln CAA | Asn AAT | Gln CAA | Asp GAT | Glu GAG | Ala GCA | Gln CAG | Lys AAG | Met ATG | 340 1020 |

FIG. 2C

| | | | | | | | | | | | | |
|---|---|---|---|---|---|---|---|---|---|---|---|---|
| Lys AAG | Asp GAT | Leu CTC | Gly GGT | Glu GAG | Leu CTA | Arg CGG | Ala GCA | Ser TCA | Tyr TAT | Gly GGA | Trp TGG | Gln CAA | Asp GAC | Thr ACT | Tyr TAT | Val GTT | Phe TTC | Thr 360<br>ACC 1080 |
| Lys AAA | Ala GCA | Met ATG | Gly GGT | Glu GAG | Met ATG | Met ATG | Ile ATC | Asn AAT | Ser AGC | Thr ACT | Arg CGA | Gly GGA | Asp GAC | Val GTA | Pro CCT | Val GTT | Ile ATT | Ile 380<br>ATA 1140 |
| Arg AGG | Pro CCT | Ser AGC | Val GTC | Ile ATC | Glu GAA | Ser AGC | Thr ACT | Tyr TAC | Lys AAA | Asp GAT | Pro CCT | Phe TTC | Pro CCT | Asp GAC | Val GTT | Glu GAA | Gly GGA | Asn 400<br>AAC 1200 |
| Arg AGG | Met ATG | Met ATG | Asp GAT | Pro CCT | Ile ATA | Val GTT | Leu TTA | Cys TGT | Tyr TAC | Gly GGG | Lys AAG | Gln CAA | Leu CTC | Thr ACG | Gly GGG | Phe TTT | Leu TTG | Val 420<br>GTT 1260 |
| Asp GAT | Pro CCA | Lys AAA | Gly GGA | Val GTT | Leu CTT | Asp GAT | Val GTA | Pro CCT | Ala GCT | Asp GAT | Met ATG | Met ATG | Val GTT | Asn AAT | Ala GCA | Thr ACG | Leu TTA | Ala 440<br>GCT 1320 |
| Ala GCT | Lys AAG | His CAT | Gly GGA | Met ATG | Ala GCA | Met ATG | Ser TCA | Pro CCT | Ser GCT | Asp GAT | Pro CCG | Glu GAA | Ile ATA | Asn AAC | Val GTG | Leu CTT | Tyr TAT | Gln 460<br>CAG 1380 |
| Ile ATC | Ala GCT | Ser TCT | Ser TCG | Ala GCG | Ile ATA | Asn AAC | Pro CCG | Leu CTG | Val GTT | Phe TTC | Lys AAA | Ser TCT | Glu GAA | Ala GCG | Ile ATT | Met ATG | Val GTG | Arg 480<br>CGT 1440 |
| His CAC | Tyr TAC | Lys AAA | Thr ACA | Ser TCC | Pro CCA | Met ATG | Cys TGC | Met ATG | Asp GAC | Val GTT | Lys AAA | Gly GGT | Asp GAT | Asp GAT | Met ATG | Val GTG | Arg CGT | Leu 500<br>TTG 1500 |
| Lys AAA | Leu CTT | Phe TTC | Asn AAT | Ser TCC | Val GTT | Asp GAT | Asp GAT | Phe TTC | Ser TCG | His CAT | Leu TTG | Trp TGG | Arg AGA | Asp GAT | Ala GCT | Gln CAA | Glu GAA | Arg 520<br>CGG 1560 |

| Ser AGT | Gly GGG | Leu TTG | Met ATG | Ser AGT | Gly GGT | Met ATG | Ser AGT | Ala GCG | Asp GAT | Ser AGT | Lys AAG | Met ATG | Met ATG | Gln CAG | Lys AAG | Leu CTA | Lys AAG | Phe TTT | 540 1620 |
| Ile ATA | Cys TGC | Lys AAG | Lys AAA | Ser TCT | Val GTT | Glu GAA | Gln CAA | Ala GCC | Lys AAA | Leu CTT | Ala GCT | Thr ACT | Ile ATT | Tyr TAT | Glu GAG | Pro CCA | Tyr TAC | Thr ACT | 560 1680 |
| Phe TTC | Tyr TAT | Lys AAG | Lys GGA | Arg AGA | Phe TTT | Asp GAT | Asn AAC | Ser AGC | Asn AAT | His CAC | Arg AGA | Leu TTA | Met ATG | Glu GAG | Asn AAT | Met ATG | Ser TCA | Glu GAG | 580 1740 |
| Asp GAC | Glu GAG | Lys AAG | Arg AGA | Glu GAA | Phe TTT | Gly GGA | Phe TTT | Asp GAT | Val GTT | Gly GGA | Ile ATT | Asn AAC | Trp TGG | Thr ACG | Asp GAC | Tyr TAC | Ile ATT | Thr ACA | 600 1800 |
| Asn AAC | Val GTT | His CAC | Ile ATT | Pro CCC | Gly GGT | Leu TTA | Arg AGA | Arg AGG | His CAT | Val GTC | Lys AAA | Leu TTG | Gly GGA | Arg AGA | Ala GCT | * TAA | | 620 1860 |
| TCA | CTA | AAC | CAG | ACC | AAA | CAG | AAT | CGA | TCC | CTT | TTA | TCT | TTT | TTT | TAT | CTT | CTT | ATC TTT | 1920 |
| TCA | TTA | CGT | GTA | ATC | GCG | TTG | TGT | CTA | ATA | TAT | CTC | GAT | TTG | TAA | TAA | TAA | GAA | AAA | 1980 |
| AAC | CGG | AAA | TGT | TGT | TAT | TGT | TAA | GTT | TGC | CCA | AAA | ATA | GTC | ATG | GAT | TTC | TCA | AGA | 2040 |
| CAA | AAA | AAA | AAA- | 3' | 2055 | | | | | | | | | | | | | | |

FIG. 2D

MS2 Promoter

```
   1 GATCTAAGACAAAAACGTGGCCATTTGCTAATTGTTGTTTTGTTGTAGCAATAACCTTA   60
  61 GTCAAAGGATTTTGTTTATTGCGGACCCAAGTTGGTTGGTCGGCTCTTGCTTAAACCACA  120
 121 TTTGGAATTTGTTGTTCTGGAGTCTGGAGATCATTGAAACACAACCAAGAAGATAGCGCA  180
 181 CTGGTTTTAAAGTCGTATGTGTAGTTCTTTGTTCACCACGAGTTTAAGGTTCTCTTTCAT  240
 241 GTCTCATTGTTCTAAATATTCATCTTCGGTTGCATGTTTAACTTCATAGTCCAGTTTATA  300
 301 TTTTCCATCTAGATGATTGGGAACATTTTGCTTACTTTTATGATCTTAAACAGATGAACG  360
 361 GTCTCATGTTAACAACATAGTACTCTTGACTTCATGATAATTTCATATCATCTAATGACT  420
 421 AAATTCTTTGCAGAGTTTAATGGTGTTGATTGTTGAAACAAGAGCAGATTGGTCAATCAC  480
 481 TACAGAAAAAAAAAAGTTGGTAACATGTAAGTTTAACGTTATTTAATAAAGGAGGATCTA  540
 541 AGTTTTCTACAAAAGCTATAATTTTTATGATGACCATATAATCCTCAAACCCTTCAAGAT  600
 601 GTGATGTGAATTATCTAAATCCCAACACGAAGAAATGAGATTTTTTAAAGTTAGCTATTT  660
 661 ATCCTTAGTTGATTTCTTAATTATAGGGTAATGGCAATATTTTTTGGAACTGATAATACG  720
 721 TTTCTTTTTTTTTTCTGAATTCTAGATGATCACGTGTAGGAAACTGATAAAATGTTGGAA  780
 781 AGAATTCGTAAGGCAATCTTTTATTTCACTTGATTTTTAAAATATTTATTTGCCTATAAA  840
 841 ACAGAGGAAGTTTTTCATCATCTTTTGTCCTTAGAACTAACCAATCTTTCATTCCTCTTA  900
 901 TAAAAACAAAACCTACTTTACTTGTCTCTTAACGATAACAAAATAACAAATAATTAATTC  960
 961 TGTTCTTGGTTTACTTAATCTTCTTTCTAGTTAAGTATATTCTTGTTGCTCATCACCAAA 1020
1021 GGTATGCTTTCTAGGTTAAGTATATTACAAGTCACCAATTTCTTAACCAACAAGCTT    1077
```

FIG. 3

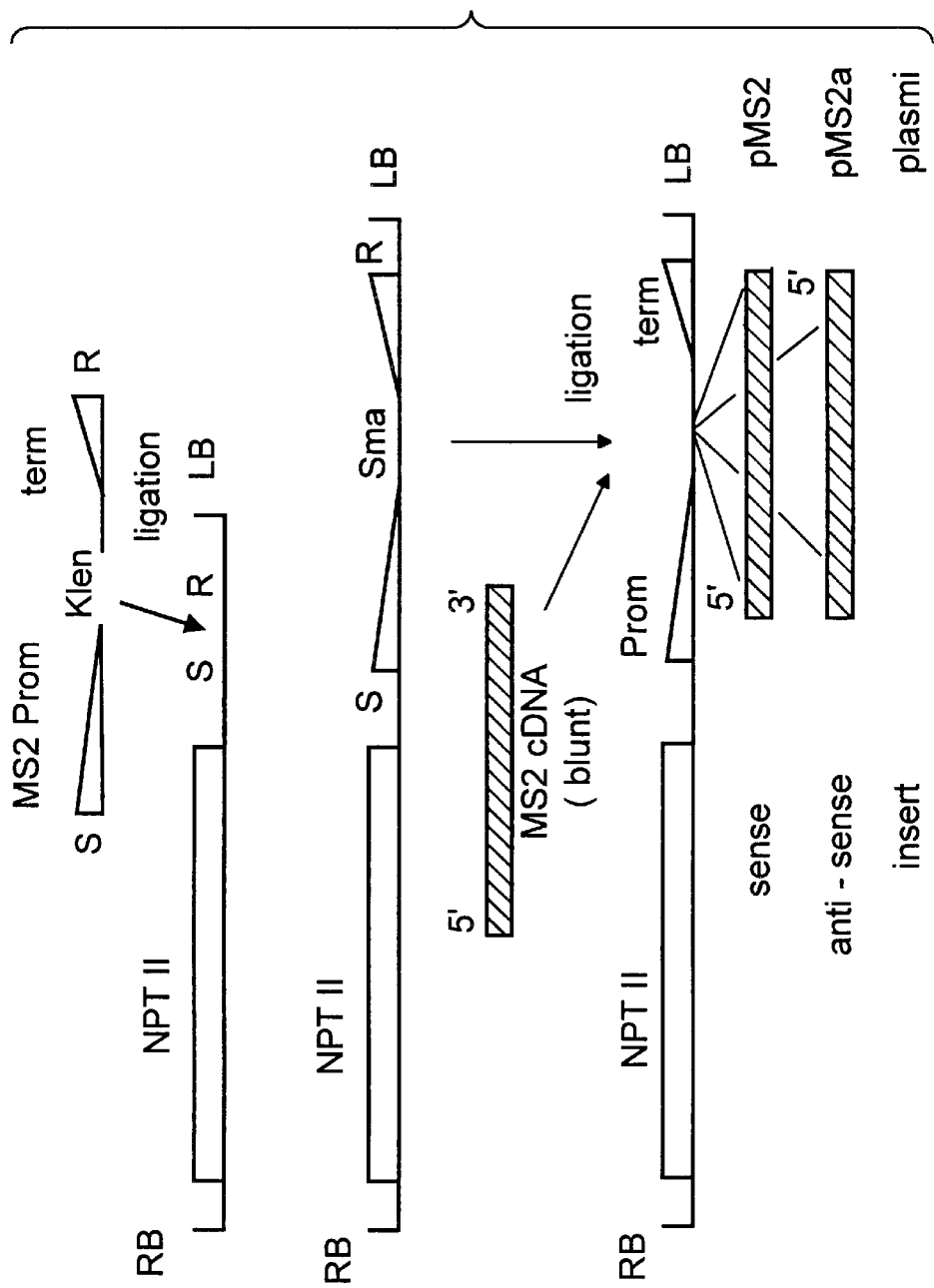
F I G. 6

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2126 base pairs
      (B) TYPE: nucleic acid
      (C) STRANDEDNESS: single
      (D) TOPOLOGY: linear (ii) MOLECULE TYPE: cDNA (iii) HYPOTHETICAL: YES (iv) ANTI-SENSE: NO (vi) ORIGINAL SOURCE:
      (A) ORGANISM: Arabidopsis thaliana (ix) FEATURE:
      (A) NAME/KEY: CDS
      (B) LOCATION:72..1919
      (D) OTHER INFORMATION:/codon_start= 72

(x) PUBLICATION INFORMATION:
      (A) AUTHORS: Stiekema Dr., W.
      (G) DATE: 1993

(xi) SEQUENCE DESCRIPTION: SEQ ID NO: 1:

```
ATTCTGTTCT TGGTTTACTT AATCTTCTTT CTAGTTAAGT ATATTCTTGT TGCTCATCAC         60

CAAAGCTTGT G ATG GAG GCT CTC TTC TTG AGT TCT TCT TCT TCC TCC ATT         110
             Met Glu Ala Leu Phe Leu Ser Ser Ser Ser Ser Ser Ile
              1               5                  10

GTA GGG TCA AAC AAG CTT ACT AGG TTA CAC AAC CAT TGT GTC TGG TCT          158
Val Gly Ser Asn Lys Leu Thr Arg Leu His Asn His Cys Val Trp Ser
 15              20                  25

ACA GTG ATT AGA GAT AAG AAA AGG TTC GGT CCC ACT TGG TGC CGT GTA          206
Thr Val Ile Arg Asp Lys Lys Arg Phe Gly Pro Thr Trp Cys Arg Val
 30              35                  40                  45

GGT GGT GGT GGT GAT GGT GGG AGA AAC AGT AAC GCA GAG AGT CCT ATT          254
Gly Gly Gly Gly Asp Gly Gly Arg Asn Ser Asn Ala Glu Ser Pro Ile
                 50                  55                  60

CGG GTT TCT TCG CTT TTG AAA GAC AGA GGT CAG GTA CTG ATT AGG GAA          302
Arg Val Ser Ser Leu Leu Lys Asp Arg Gly Gln Val Leu Ile Arg Glu
                 65                  70                  75

CAG AGT TCG CCG GCT ATG GAT GCT GAG ACA TTG GTT CTG TCT CCA AAC          350
Gln Ser Ser Pro Ala Met Asp Ala Glu Thr Leu Val Leu Ser Pro Asn
             80                  85                  90

GGG AAT GGG AGA ACC ATT GAG ATC AAT GGA GTA AAG ACT TTG ATG CCT          398
Gly Asn Gly Arg Thr Ile Glu Ile Asn Gly Val Lys Thr Leu Met Pro
 95                 100                 105

TTT AGT GGC GCT TCT ATG GTG GGG ATG AAA GAA GGA CTT GGC ATA ATC          446
Phe Ser Gly Ala Ser Met Val Gly Met Lys Glu Gly Leu Gly Ile Ile
110                 115                 120                 125

AGT TTC CTC CAA GGG AAG AAG TTT CTA ATC ACT GGC TCG ACC GGT TTC          494
Ser Phe Leu Gln Gly Lys Lys Phe Leu Ile Thr Gly Ser Thr Gly Phe
                130                 135                 140
```

-continued

| | |
|---|---|
| TTA GCT AAA GTA CTG ATT GAG AAA GTC TTG AGA ATG GCT CCT GAT GTC<br>Leu Ala Lys Val Leu Ile Glu Lys Val Leu Arg Met Ala Pro Asp Val<br>              145                        150                        155 | 542 |
| AGC AAG ATA TAT CTC TTG ATT AAA GCC AAA AGC AAA GAA GCT GCG ATC<br>Ser Lys Ile Tyr Leu Leu Ile Lys Ala Lys Ser Lys Glu Ala Ala Ile<br>              160                        165                        170 | 590 |
| GAG CGG CTA AAG AAC GAG GTG TTA GAT GCA GAG CTT TTT AAT ACT CTA<br>Glu Arg Leu Lys Asn Glu Val Leu Asp Ala Glu Leu Phe Asn Thr Leu<br>175                        180                        185 | 638 |
| AAA GAG ACT CAT GGA GCA TCT TAC ATG TCT TTC ATG TTA ACT AAA CTC<br>Lys Glu Thr His Gly Ala Ser Tyr Met Ser Phe Met Leu Thr Lys Leu<br>190                        195                        200                        205 | 686 |
| ATC CCT GTG ACC GGA AAC ATT TGC GAT TCA AAC ATT GGG TTG CAA GCA<br>Ile Pro Val Thr Gly Asn Ile Cys Asp Ser Asn Ile Gly Leu Gln Ala<br>              210                        215                        220 | 734 |
| GAT TCA GCT GAA GAG ATT GCG AAA GAA GTT GAT GTT ATA ATC AAT TCT<br>Asp Ser Ala Glu Glu Ile Ala Lys Glu Val Asp Val Ile Ile Asn Ser<br>                    225                        230                        235 | 782 |
| GCT GCT AAT ACA ACC TTC AAT GAA AGA TAC GAT GTT GCT CTG GAC ATC<br>Ala Ala Asn Thr Thr Phe Asn Glu Arg Tyr Asp Val Ala Leu Asp Ile<br>              240                        245                        250 | 830 |
| AAC ACA AGA GGG CCC GGT AAT CTC ATG GGA TTC GCC AAG AAG TGC AAG<br>Asn Thr Arg Gly Pro Gly Asn Leu Met Gly Phe Ala Lys Lys Cys Lys<br>255                        260                        265 | 878 |
| AAA CTC AAA CTG TTC TTG CAA GTA TCC ACA GCT TAT GTG AAC GGA CAA<br>Lys Leu Lys Leu Phe Leu Gln Val Ser Thr Ala Tyr Val Asn Gly Gln<br>270                        275                        280                        285 | 926 |
| AGA CAA GGA AGG ATC ATG GAG AAG CCA TTT TCT ATG GGA GAT TGT ATA<br>Arg Gln Gly Arg Ile Met Glu Lys Pro Phe Ser Met Gly Asp Cys Ile<br>                    290                        295                        300 | 974 |
| GCA ACA GAG AAC TTC CTC GAA GGA AAC AGA AAA GCA TTA GAT GTT GAT<br>Ala Thr Glu Asn Phe Leu Glu Gly Asn Arg Lys Ala Leu Asp Val Asp<br>                    305                        310                        315 | 1022 |
| AGA GAG ATG AAG TTA GCT CTT GAA GCT GCT AGA AAA GGG ACT CAA AAT<br>Arg Glu Met Lys Leu Ala Leu Glu Ala Ala Arg Lys Gly Thr Gln Asn<br>              320                        325                        330 | 1070 |
| CAA GAT GAG GCA CCG AAG ATG AAG GAT CTC GGT CTA GAG CGG GCA AGA<br>Gln Asp Glu Ala Pro Lys Met Lys Asp Leu Gly Leu Glu Arg Ala Arg<br>335                        340                        345 | 1118 |
| TCA TAT GGA TGG CAA GAC ACT TAT GTT TTC ACC AAA GCA ATG GGT GAG<br>Ser Tyr Gly Trp Gln Asp Thr Tyr Val Phe Thr Lys Ala Met Gly Glu<br>350                        355                        360                        365 | 1166 |
| ATG ATG ATC AAT AGC ACT CGA GGA GAC GTA CCT GTT GTT ATT ATA AGG<br>Met Met Ile Asn Ser Thr Arg Gly Asp Val Pro Val Val Ile Ile Arg<br>                    370                        375                        380 | 1214 |
| CCT AGC GTC ATC GAA AGC ACT TAC AAA GAT CCT TTC CCT GGA TGG ATG<br>Pro Ser Val Ile Glu Ser Thr Tyr Lys Asp Pro Phe Pro Gly Trp Met<br>              385                        390                        395 | 1262 |
| GAA GGA AAC AGG ATG ATG GAT CCT ATA GTT TTA TGT TAC GGG AAG GGG<br>Glu Gly Asn Arg Met Met Asp Pro Ile Val Leu Cys Tyr Gly Lys Gly<br>              400                        405                        410 | 1310 |
| CAA CTC ACG GGG TTT TTG GTT GAT CCA AAA GGA GTT CTT GAT GTA GTT<br>Gln Leu Thr Gly Phe Leu Val Asp Pro Lys Gly Val Leu Asp Val Val<br>415                        420                        425 | 1358 |
| CCT GCT GAT ATG GTT GTT AAT GCA ACG TTA GCT GCT ATA GCA AAG CAT<br>Pro Ala Asp Met Val Val Asn Ala Thr Leu Ala Ala Ile Ala Lys His<br>430                        435                        440                        445 | 1406 |
| GGA ATG GCA ATG TCA GAT CCG GAA CCT GAA ATA AAC GTG TAT CAG ATC<br>Gly Met Ala Met Ser Asp Pro Glu Pro Glu Ile Asn Val Tyr Gln Ile<br>                    450                        455                        460 | 1454 |

```
GCT TCT TCG GCG ATA AAC CCG CTG GTT TTC GAA GAC TTA GCG GAG CTT    1502
Ala Ser Ser Ala Ile Asn Pro Leu Val Phe Glu Asp Leu Ala Glu Leu
            465                 470                 475

CTT TAT AAC CAC TAC AAA ACA TCC CCA TGC ATG GAC TCT AAA GGT GAT    1550
Leu Tyr Asn His Tyr Lys Thr Ser Pro Cys Met Asp Ser Lys Gly Asp
        480                 485                 490

CCT ATT ATG GTG CGT TTG ATG AAA CTT TTC AAT TCC GTT GAT GAT TTC    1598
Pro Ile Met Val Arg Leu Met Lys Leu Phe Asn Ser Val Asp Asp Phe
495                 500                 505

TCG GAT CAT TTG TGG AGA GAT GCT CAA GAA CGG AGT GGG TTG ATG AGT    1646
Ser Asp His Leu Trp Arg Asp Ala Gln Glu Arg Ser Gly Leu Met Ser
510                 515                 520                 525

GGT ATG AGT TCA GCG GAT AGT AAG ATG ATG CAG AAG CTA AAG TTT ATA    1694
Gly Met Ser Ser Ala Asp Ser Lys Met Met Gln Lys Leu Lys Phe Ile
                530                 535                 540

TGC AAG AAA TCT GTT GAA CAA GCC AAA CAC CTT GCT ACT ATT TAT GAG    1742
Cys Lys Lys Ser Val Glu Gln Ala Lys His Leu Ala Thr Ile Tyr Glu
            545                 550                 555

CCA TAC ACT TTC TAT GGT GGA AGA TTT GAT AAC AGC AAT ACA CAG AGA    1790
Pro Tyr Thr Phe Tyr Gly Gly Arg Phe Asp Asn Ser Asn Thr Gln Arg
        560                 565                 570

TTA ATG GAG AAT ATG TCA GAG GAC GAG AAG AGA GAA TTT GGA TTT GAT    1838
Leu Met Glu Asn Met Ser Glu Asp Glu Lys Arg Glu Phe Gly Phe Asp
575                 580                 585

GTT GGA AGC ATT AAC TGG ACG GAC TAC ATT ACA AAC GTT CAC ATT CCC    1886
Val Gly Ser Ile Asn Trp Thr Asp Tyr Ile Thr Asn Val His Ile Pro
590                 595                 600                 605

GGT TTA AGA AGG CAT GTC TTG AAA GGA AGA GCT TAACTTTGAA TCTCACTAAA   1939
Gly Leu Arg Arg His Val Leu Lys Gly Arg Ala
                610                 615

CCAGACCAAA CAGAATCGAT CCCTTCTTTT ATCTTTTTAT CTTTTTCTTT TTTCATTACG   1999

TGTAATCGCG TTGTGTCTAA TATATCAGCT CGATTTGTAA TAATTTGAAA AAACCGGAA    2059

ATGTTGTTAT CTTTAAGTTT GCCCAAAATC TATAGTCATG TTCGATTCAA GACAAAAAAA   2119

AAAAAAA                                                            2126

(2) INFORMATION FOR SEQ ID NO: 2:

(i) SEQUENCE CHARACTERISTICS:
        (A) LENGTH: 616 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Ala Leu Phe Leu Ser Ser Ser Ser Ser Ile Val Gly Ser
 1               5                  10                  15

Asn Lys Leu Thr Arg Leu His Asn His Cys Val Trp Ser Thr Val Ile
            20                  25                  30

Arg Asp Lys Lys Arg Phe Gly Pro Thr Trp Cys Arg Val Gly Gly Gly
        35                  40                  45

Gly Asp Gly Gly Arg Asn Ser Asn Ala Glu Ser Pro Ile Arg Val Ser
    50                  55                  60

Ser Leu Leu Lys Asp Arg Gly Gln Val Leu Ile Arg Glu Gln Ser Ser
65                  70                  75                  80

Pro Ala Met Asp Ala Glu Thr Leu Val Leu Ser Pro Asn Gly Asn Gly
                85                  90                  95

Arg Thr Ile Glu Ile Asn Gly Val Lys Thr Leu Met Pro Phe Ser Gly
            100                 105                 110
```

```
Ala Ser Met Val Gly Met Lys Glu Gly Leu Gly Ile Ile Ser Phe Leu
        115                 120                 125
Gln Gly Lys Lys Phe Leu Ile Thr Gly Ser Thr Gly Phe Leu Ala Lys
    130                 135                 140
Val Leu Ile Glu Lys Val Leu Arg Met Ala Pro Asp Val Ser Lys Ile
145                 150                 155                 160
Tyr Leu Leu Ile Lys Ala Lys Ser Lys Glu Ala Ala Ile Glu Arg Leu
                165                 170                 175
Lys Asn Glu Val Leu Asp Ala Glu Leu Phe Asn Thr Leu Lys Glu Thr
            180                 185                 190
His Gly Ala Ser Tyr Met Ser Phe Met Leu Thr Lys Leu Ile Pro Val
        195                 200                 205
Thr Gly Asn Ile Cys Asp Ser Asn Ile Gly Leu Gln Ala Asp Ser Ala
    210                 215                 220
Glu Glu Ile Ala Lys Glu Val Asp Val Ile Ile Asn Ser Ala Ala Asn
225                 230                 235                 240
Thr Thr Phe Asn Glu Arg Tyr Asp Val Ala Leu Asp Ile Asn Thr Arg
                245                 250                 255
Gly Pro Gly Asn Leu Met Gly Phe Ala Lys Lys Cys Lys Lys Leu Lys
            260                 265                 270
Leu Phe Leu Gln Val Ser Thr Ala Tyr Val Asn Gly Gln Arg Gln Gly
        275                 280                 285
Arg Ile Met Glu Lys Pro Phe Ser Met Gly Asp Cys Ile Ala Thr Glu
        290                 295                 300
Asn Phe Leu Glu Gly Asn Arg Lys Ala Leu Asp Val Asp Arg Glu Met
305                 310                 315                 320
Lys Leu Ala Leu Glu Ala Ala Arg Lys Gly Thr Gln Asn Gln Asp Glu
                325                 330                 335
Ala Pro Lys Met Lys Asp Leu Gly Leu Glu Arg Ala Arg Ser Tyr Gly
            340                 345                 350
Trp Gln Asp Thr Tyr Val Phe Thr Lys Ala Met Gly Glu Met Met Ile
        355                 360                 365
Asn Ser Thr Arg Gly Asp Val Pro Val Val Ile Ile Arg Pro Ser Val
    370                 375                 380
Ile Glu Ser Thr Tyr Lys Asp Pro Phe Pro Gly Trp Met Glu Gly Asn
385                 390                 395                 400
Arg Met Met Asp Pro Ile Val Leu Cys Tyr Gly Lys Gly Gln Leu Thr
                405                 410                 415
Gly Phe Leu Val Asp Pro Lys Gly Val Leu Asp Val Val Pro Ala Asp
            420                 425                 430
Met Val Val Asn Ala Thr Leu Ala Ala Ile Ala Lys His Gly Met Ala
        435                 440                 445
Met Ser Asp Pro Glu Pro Glu Ile Asn Val Tyr Gln Ile Ala Ser Ser
    450                 455                 460
Ala Ile Asn Pro Leu Val Phe Glu Asp Leu Ala Glu Leu Leu Tyr Asn
465                 470                 475                 480
His Tyr Lys Thr Ser Pro Cys Met Asp Ser Lys Gly Asp Pro Ile Met
                485                 490                 495
Val Arg Leu Met Lys Leu Phe Asn Ser Val Asp Asp Phe Ser Asp His
            500                 505                 510
Leu Trp Arg Asp Ala Gln Glu Arg Ser Gly Leu Met Ser Gly Met Ser
        515                 520                 525
Ser Ala Asp Ser Lys Met Met Gln Lys Leu Lys Phe Ile Cys Lys Lys
```

```
                530                  535                 540
Ser Val Glu Gln Ala Lys His Leu Ala Thr Ile Tyr Glu Pro Tyr Thr
545                 550                 555                 560

Phe Tyr Gly Gly Arg Phe Asp Asn Ser Asn Thr Gln Arg Leu Met Glu
                565                 570                 575

Asn Met Ser Glu Asp Glu Lys Arg Glu Phe Gly Phe Asp Val Gly Ser
                580                 585                 590

Ile Asn Trp Thr Asp Tyr Ile Thr Asn Val His Ile Pro Gly Leu Arg
                595                 600                 605

Arg His Val Leu Lys Gly Arg Ala
            610                 615
```

(2) INFORMATION FOR SEQ ID NO: 3:

(i) SEQUENCE CHARACTERISTICS:
        (A) LENGTH: 1077 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:1057..1077
        (D) OTHER INFORMATION:/partial
            /codon_start= 1057

(xi) SEQUENCE DESCRIPTION: SEQ ID NO: 3:

```
GATCTAAGAC AAAAACGTGG CCATTTGCTA ATTGTTGTTT TTGTTGTAGC AATAACCTTA      60

GTCAAAGGAT TTTGTTTATT GCGGACCCAA GTTGGTTGGT CGGCTCTTGC TTAAACCACA     120

TTTGGAATTT GTTGTTCTGG AGTCTGGAGA TCATTGAAAC ACAACCAAGA AGATAGCGCA     180

CGTGTTTTAA AGTCGTATGT GTAGTTCTTT GTTCACCACG AGTTTAAGGT TCTCTTTCAT     240

GTCTCATTGT TCTAAATATT CATCTTCGGT TGCATGTTTA ACTTCATAGT CCAGTTTATA     300

TTTTCCATCT AGATGATTGG GAACATTTTG CTTACTTTTA TGATCTTAAA CAGATGAACG     360

GTCTCATGTT AACAACATAG TACTGTTGAC TTCATGATAA TTTCATATCA TCTAATGACT     420

AAATTCTTTG CAGAGTTTAA TGGTGTTGAT TGTTGAAACA AGAGCAGATT GGTCAATCAC     480

TACAGAAAAA AAAAAGTTGG TAACATGTAA GTTTAACGTT ATTTAATAAA GGAGGATCTA     540

AGTTTTCTAC AAAAGCTATA ATTTTTATGA TGACCATATA ATCCTCAAAC CCTTCAAGAT     600

GTGATGTGAA TTATCTAAAT CCCAACACGA AGAAATGAGA TTTTTTAAAG TTAGCTATTT     660

ATCCTTAGTT GATTTCTTAA TTATAGGGTA ATGGCAATAT TTTTTGGAAC TGATAATACG     720

TTTCTTTTTT TTTTCTGAAT TCTAGATGAT CACGTGTAGG AAACTGATAA AATGTTGGAA     780

AGAATTCGTA AGGCAATCTT TTATTTCACT TGATTTTTAA AATATTTATT TGCCTATAAA     840

ACAGAGGAAG TTTTTCATCA TCTTTTGTCC TTAGAACTAA CCAATCTTTC ATTCCTCTTA     900

TAAAACAAA ACCTACTTTA CTTGTCTCTT AACGATAACA AAATAACAAA TAATTAATTC     960

TGTTCTTGGT TTACTTAATC TTCTTTCTAG TTAAGTATAT TCTTGTTGCT CATCACCAAA    1020

GGTATGCTTT CTAGGTTAAG TATATTACAA GTCACC AAT TTC TTA ACC AAC AAG     1074
                                         Asn Phe Leu Thr Asn Lys
                                          1               5

CTT                                                                  1077
Leu
```

(2) INFORMATION FOR SEQ ID NO: 4:

```
    (i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 4:

Asn Phe Leu Thr Asn Lys Leu
  1               5
```

METHOD FOR OBTAINING MALE-STERILE PLANTS

FIELD OF THE INVENTION

The invention involves genetic manipulation of plants by the application of recombinant DNA technology. The invention describes a method for obtaining plants which display nuclear encoded male-sterility, due to expression of said recombinant DNA as well as parts of said plants which are either sexually or asexually reproducible, or both.

BACKGROUND OF THE ART

Heterosis is the effect that progeny obtained through cross-pollination show better agronomical properties than progeny derived through self-pollination. These better properties result in a higher profit which is the reason that the development of hybrid seed is one of the prime objectives for the seed industry.

To obtain hybrid seeds it is necessary that the female plants are unable to self-pollinate. Many crop plants accommodate both the female and male reproductive organs on the same individual and thus self-pollination is dominating cross-pollination. Introduction of male sterility in many crops is thus necessary for hybrid seed production.

In production fields the male-sterile acceptor and male-fertile donor plants are grown side by side and after cross-pollination the hybrid seed is harvested. Hybrid seed is separately collected from the non-hybrid seeds formed on the donor plants by destruction of these male-fertile plants before the harvest. This approach makes the discrimination between fertile and sterile plants necessary which can be accomplished by the appearance of different phenotypes. Also a selectable marker gene such as a gene coding for a herbicide resistance, closely linked to the male-sterility locus can be used for this purpose. Selection of the hybrid seeds can than be accomplished by spraying the herbicide, which will result in the destruction of the male-fertile plants. Alternatively the hybrid seeds can be selected after harvesting by a phenotypic marker expressed at the seed level.

Nowadays in agricultural practice male-sterile parental lines are obtained by physically emasculation of the plants or by the application of cytoplasmic or nuclear encoded male-sterile mutants. There are only a limited number of natural male-sterile mutants available in the commercial interesting crops. This renders the latter approach often not feasible. In addition naturally male-sterile plants have their disadvantages. There preparation is laborious and there maintenance and propagation difficult. They often show additional, detrimental traits and a difficult inheritance.

The development of nuclear encoded male-sterile plants by the application of recombinant DNA techniques has succeeded in new approaches which circumvent most of the disadvantages mentioned above.

STATE OF THE ART

The International Patent Application WO92/18625, MOGEN International N.V. proposes methods for the production of restorable male-sterile plants in general terms, essentially comprising integration of a recombinant polynucleotide into their genome, essentially comprising an inhibitory gene, which, upon proper expression in the anthers of the plant, is capable of inhibiting expression of one or more genes encoding an enzyme involved in the synthesis of chalcone, or one of its precursors.

DEFINITIONS

Antisense gene: a nucleotide sequence having a homology of more than 50%, preferably more than 80% with a target gene as defined herein, and which is linked to a promotor in 3' to 5' orientation with respect to the target gene and can be expressed as an RNA molecule.

Gene or sense gene: a nucleotide sequence that can be expressed as RNA molecule and/or polypeptide.

Promoter: a nucleotide sequence which directs the expression of a (sense-) gene or antisense gene, or nucleotide sequences derived thereof.

Inhibitor gene: a (sense-)gene or antisense gene, expression of which leads to prevention or inhibition of the expression of a target gene as defined herein.

Repair gene: a gene capable to prevent or sufficiently inhibit the action of an inhibitor gene thus repairing the activity of a target gene.

Target gene: a gene which activity is to be inhibited by proper expression of an inhibitor gene as herein defined.

SUMMARY OF THE INVENTION

The present invention describes the male-sterile *Arabidopsis thaliana* mutant PA and the molecular isolation and analysis of the gene, called MS2 (FIG. 1). Mutation of this gene is responsible for the male-sterile phenotype of PA. The only other male sterile mutant of *Arabidopsis thaliana*, ms1, has been reported by Van der Veen and Wirtz (1968). This mutant was obtained by classical mutagenesis and is the only other male sterility mutant described in the literature, which does not show pleiotropic effects. Further molecular characterization of ms1 has not been reported so no information is available on the nature of the male-sterility gene.

Accordingly, the present invention provides a gene isolated from the cDNA library of a plant which encodes a protein indicated as MS2 which is involved in pollen development, said gene having the nucleotide sequence as shown in FIG. 2 or a homologous gene. Further, this invention provides a promoter of the MS2 gene isolated from the chromosomal DNA of a plant, said promoter having the nucleotide sequence as shown in FIG. 3 or a homologous promoter.

Further, the present invention provides recombinant polynucleotides which can be suitably used for obtaining a male-sterile plant, essentially comprising:

a) an inhibitor gene capable of inhibiting expression of a target gene in the said plant, encoding the MS2 protein involved in pollen development said gene having the sequence as shown in FIG. 2 or a homologous target gene, and b) the promoter that is active in the tapetum of said plant, linked to said inhibitor gene as to achieve expression thereof in the tapetum of said plant.

In the preferred embodiment of the invention the inhibitor gene is a (sense-)gene or an antisense gene directed against the target gene. In another preferred embodiment according to the invention the promoter that is active in the tapetum of a plant comprises the promoter of the MS2 gene, said promoter having the sequence as shown in FIG. 3.

The present invention also provides a method for obtaining a male-sterile plants comprising the steps of:
a) transferring a recombinant polynucleotide according to the invention to cells of a male-fertile plant,
b) generating whole new plants from cells having incorporated said recombinant polynucleotide, and
c) selecting a plant that is male-sterile.

Yet another embodiment of the invention is a recombinant plant genome, comprising incorporated therein a recombinant polynucleotide according to the invention.

In a yet further preferred embodiment of the invention a method is provided for a cost effective production of hybrid seed, due to use of large numbers of heterozygous male-sterile plants, which have been obtained by crossing a homozygous male-sterile plant of the desired variety with a male-fertile plant of the same variety.

The invention further encompasses (hybrid) seed obtained through crossing or selfing of any of the plants according to the invention.

Other preferred embodiments of the invention are the plasmids pMS2 and pMS2as (see FIG. 6).

BRIEF DESCRIPTION OF THE FIGURES

FIG. 2: The nucleotide sequence of the MS2 mRNA.

FIG. 3: The nucleotide sequence of the promoter of the MS2 gene.

FIG. 6: A diagrammatic representation of the different cloning steps for obtaining the chimeric sense and antisense MS2 constructs and plasmids pMS2 en pMS2as.

DETAILED DESCRIPTION OF THE INVENTION

1. Isolation of the MS2 gene of *Arabidopsis thaliana*

Figure 1:
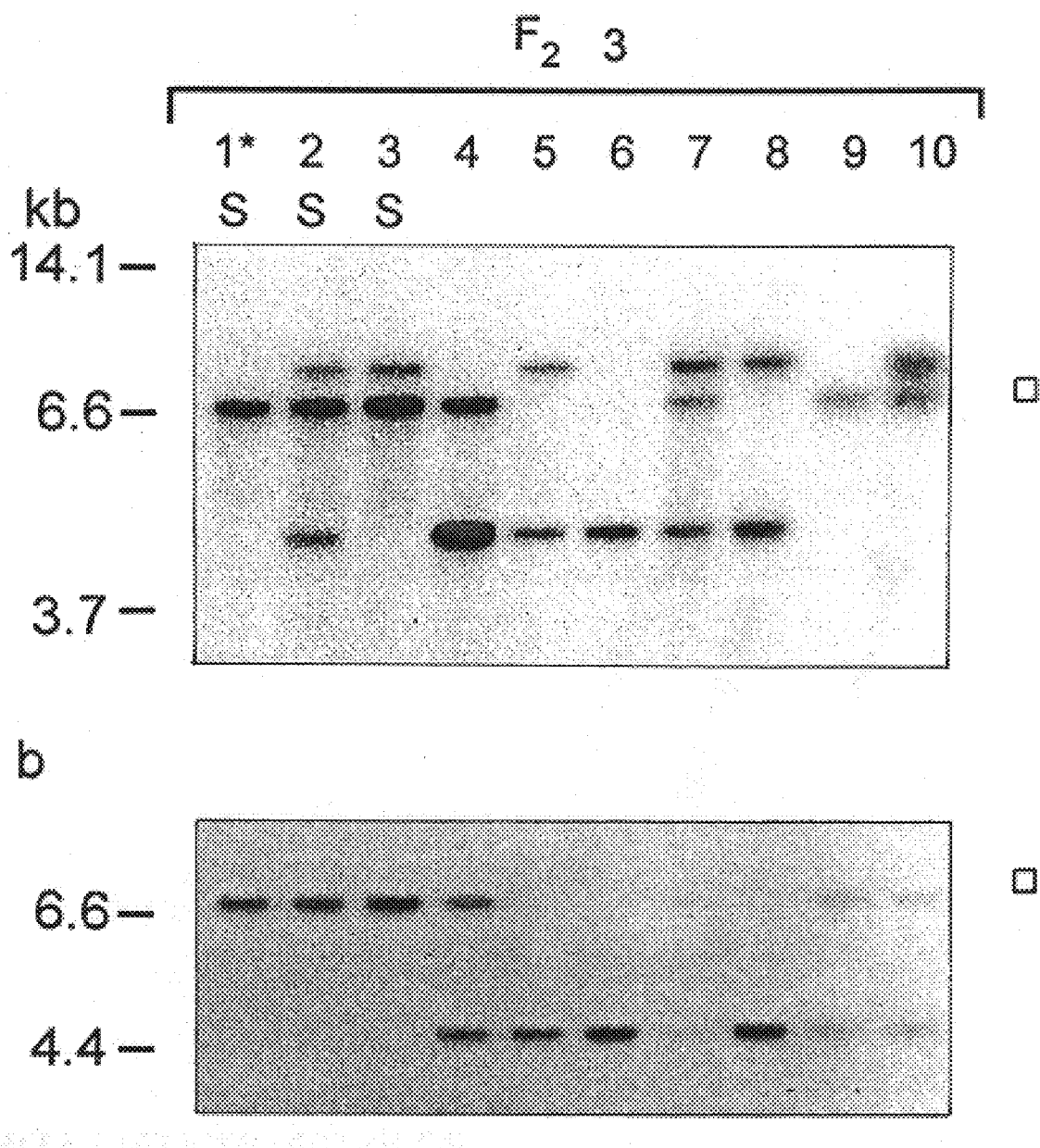
FIG. 1: Southern analysis of the progeny of a cross between the male-sterile Arabidopsis thaliana mutant PA and male-fertile *Arabidopsis thaliana* ecotype Landsberg erecta.

The maize Enhancer-Inhibitor (En-I) (Peterson, 1953), also known as Suppressor-Mutator (Spm) (McClintock, 1954), transposable element system has been used for transposon tagging of a number of genes in maize and was shown to transpose when introduced by transformation in a heterologous plant species (Masson and Federoff, 1989; Pereira and Saedler, 1989; Frey et al., 1989). We constructed a transformation vector containing three units, namely: a) an immobile En transposase source (Masson and Federoff, 1987), under control of the strong Cauliflower Mosaic Virus 35S promotor; b) a mobile I element as insertion mutagen (Schwartz-Sommer et al., 1985); c) a hygromycin phosphotransferase gene (Van den Elzen et al., 1985) conferring resistance to the antibiotic hygromycin. This 'in cis two element En-I' vector construct was used for *Agrobacterium tumefaciens* mediated transformation of *Arabidopsis thaliana* (Valvekens, 1988). A male sterile plant was found among the third generation (T3) progeny of a successively self-fertilized primary transformant (T1) with frequently transposing I elements. The plant was coded PA (Pollen Absent). As the mutation involved can be complemented by ms1, the only other male-sterile mutant without pleiotropic effects described in Arabidopsis (Van der Veen and Wirtz, 1968), we called this novel mutant ms2. Segregation analysis of the male-sterile phenotype and the I transposable element was performed as follows. DNA of F2 progenies from a cross PA x Landsberg erecta was Southern transferred and hybridized with an I element specific probe (FIG. 1). DNA was digested with HindIII which does not cut inside the I element. This F2 progeny lacked the En transposase genes and therefore all detected fragments denote stable I element inserts. A 6.6 kb I element containing fragment (■), is homozygous only in plants displaying a male sterile (ms) phenotype. Plant F2 3-1 (*) has only this ms2 accompanying I element and was therefore used for the isolation of the transposon flanking DNA by Inverse Polymerase Chain Reaction (IPCR) (Masson and Federoff, 1989; Ochman et al. 1988). The IPCR fragment was cloned, sequenced and used as a probe to isolate clones from a flower specific cDNA (Weigel et al., 1992) as well as a genomic lambda library of Arabidopsis.

Analysis of the MS2 MRNA

The cDNA clone (largest out of 3 isolated) was double-stranded sequenced using the Taq Dye Deoxy Terminator Cycle Sequencing Kit (Applied Biosystems) and an automated DNA sequencer (Applied Biosystems). Nucleotide and predicted amino-acid sequences of MS2 cDNA are shown in FIG. 2. Sequence analysis was performed using the Genetics Computer Group (GCG) software package (Devereux et.al. 1984). Nucleotides are numbered beginning with the first position of the ATG initiation triplet. A nonsense codon upstream (−36) indicates that this the translation start. The polyadenylation signal sequence (position 1967 underlined) precedes the poly(A) tail. The position of the I-element insertion (AAA) at position 1800 is underlined. The last three amino acids (Gly-Arg-Gly) contain a putative C-terminal microbody targeting signal (CMTS) suggesting a role of this part in the protein which is absent in male sterile mutant alleles due to excision footprints causing frameshifts. Data base searches (FAS-TA/BLAST) revealed homology to a DNA sequence (EMBL release 33.0, 12/92) located upstream of the wheat mitochondria 26S ribosomal RNA rrn26 gene. The region of homology in the MS2 cDNA (1040–1203) is underlined and shows 77.6% identity to the wheat mitochondrial nucleotide sequence. This region is located about 2 kbp upstream of the rrn26 gene at position 650–814 of the published sequence (Spencer et al., 1992). No function has been ascribed to this mitochondrial DNA segment which reveals an open reading frame whose predicted amino acids show 81.7% identity to the MS2 protein (55 amino-acids). The homology in the mitochondrial DNA segment does not extend beyond this region but is precisely flanked by intron-exon boundaries.

FIG. 3 shows the nucleotide sequence of the promoter of the MS2 gene. Said sequence is obtained from *A. thaliana* ecotype Landsberg erecta genomic clone of the MS2 gene. The TATA box of the MS2 gene is shown underlined (position 835) and the 5' end of the MS2 cDNA sequence is marked with an asterisk (position 957). A unique AseI restriction site (ATTAAT) at position 953 allows cloning of the promoter for further plasmid constructions described.

3. Analysis of the expression of the MS2 gene in *Arabidopsis thaliana*.

Figure 4A:
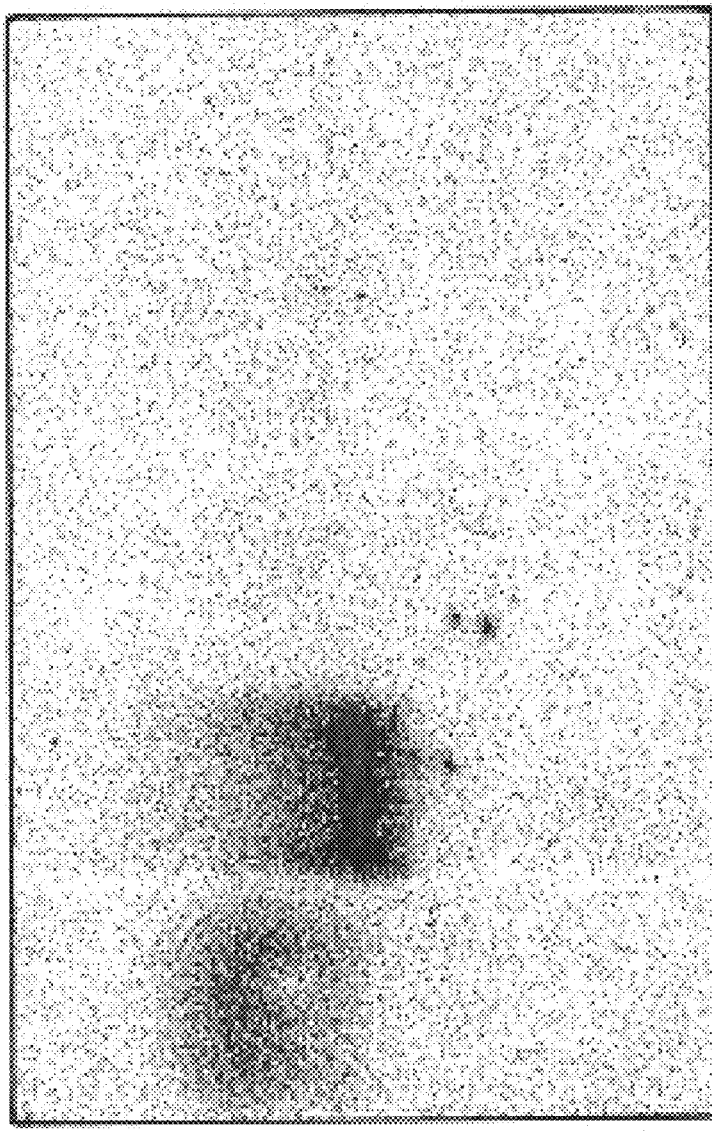
FIG. 4a: Northern analysis of the expression of the MS2 gene in different organs of *Arabidopsis thaliana*.

Northern analysis of the expression of the MS2 gene in different organs of *Arabidopsis thaliana* showed that MS2 MRNA could only be detected in flowers and siliques but not in seedlings and leaf or stem tissue (see FIG. 4a).

Figure 4B:
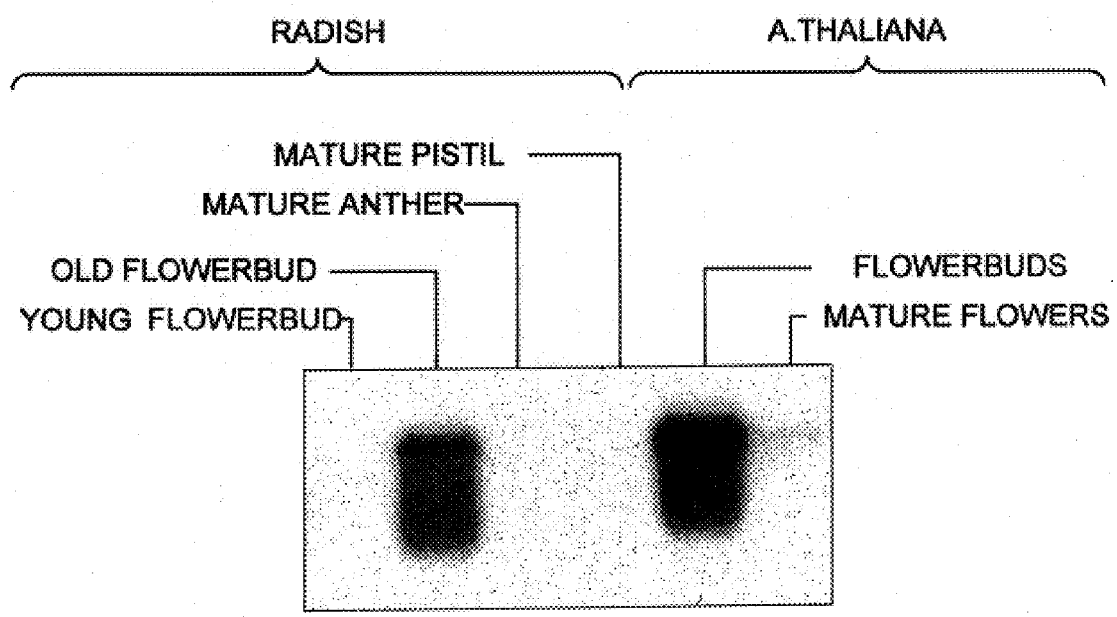
FIG. 4b: Northern analysis of the expression of the MS2 gene in different organs of *Raphanus satirus* (radish).
Figure 5:
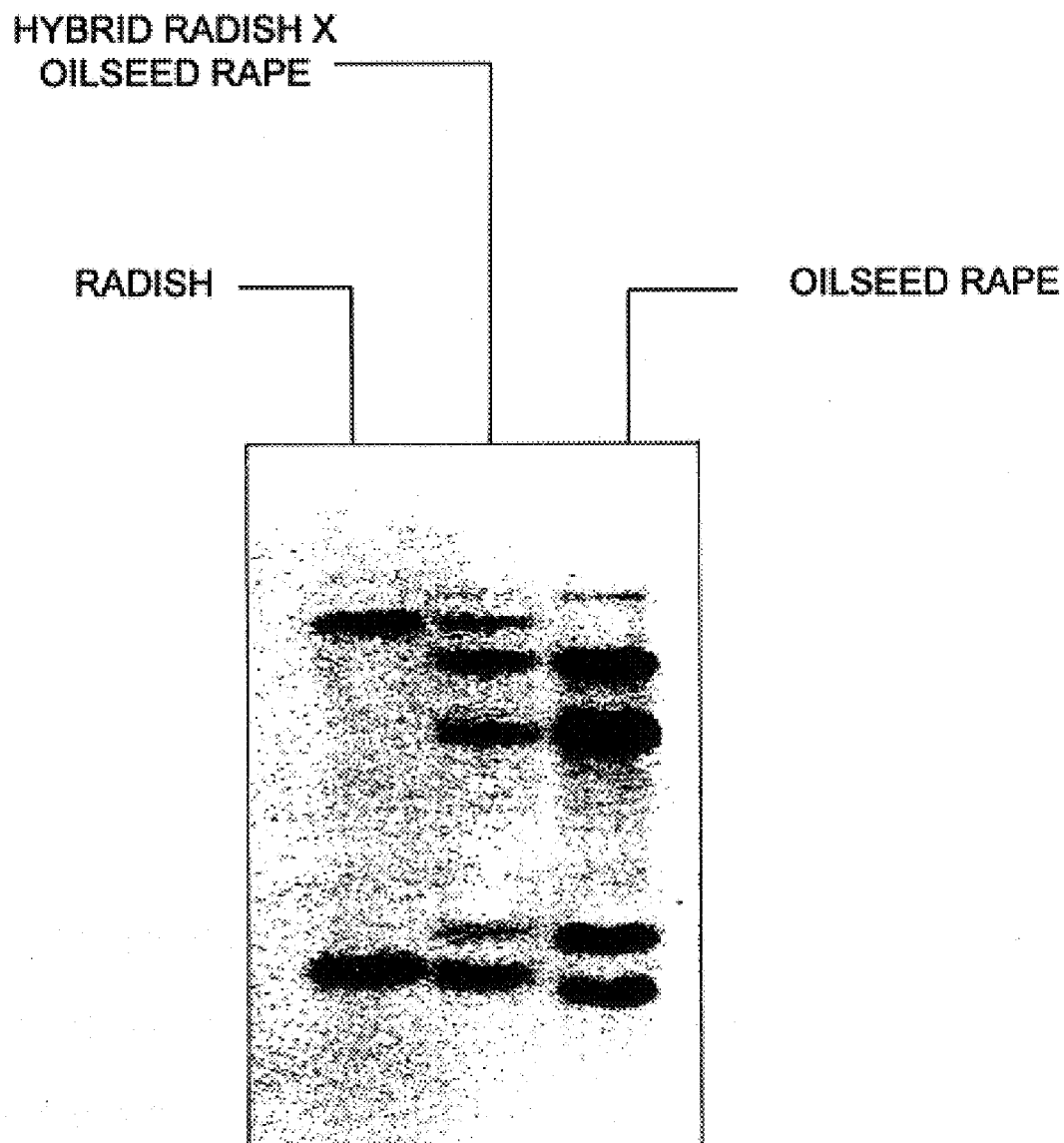
FIG. 5: Southern analysis of the presence of MS2 homologues in radish and oilseed rape.

As shown in FIG. 4b MS2 RNA could also be detected in flowerbuds of radish. By Southern blot analysis we have confirmed that MS2 homologous genes are present in radish but also in oilseed rape (FIG. 5) which indicates that male sterility can be induced in oilseed rape by sense-MS2 or antisense-MS2 expression.

4. The present invention envisages the following steps towards obtaining male-sterile plants:

A sense-MS2 or antisense-MS2 gene of *Arabidopsis thaliana* or its homologous counterpart of other species is placed under the control of the MS2 promoter, which DNA sequence is shown in FIG. 3, and these constructs can be used for the transformation of fertile crop plants. After selection of transformed plants which express the construct, and after the plants are allowed to flower, transgenic plants showing disturbed pollen development can be selected.

The diagram of FIG. 6 shows the steps of the process for preparing the above sense and antisense constructs. A binary vector (origin pBIN19), containing a chimaeric NPT II gene conferring kanamycin resistance to plant cells, with unique SalI (S) and EcoRI (R) restriction sites serves as the basic vector unit. The MS2 gene promotor and CaMV 35S poly (A) addition signal/terminator (term) are cloned after Klenow polymerase treatment (Klen). The MS2 cDNA fragment is made blunt (with Klenow polymerase) and cloned into the SmaI restriction site in two orientations with respect to the MS2 promotor (prom). This results in the two plasmids designated pMS2 (sense) and pMS2as (anti-sense). Other abbreviations used: RB=T-DNA right border; LB=T-DNA left border; 5' and 3' refer to the ends of the cDNA (coding strand) defined by unique resistriction sites in the cDNA clone.

In general nuclear encoded male-sterile plants can thus be obtained and used for hybrid seed production. Plants of a selected variety have to be genetically transformed by introducing into cells of the said plant one or more recombinant polynucleotides, essentially comprising one or more inhibitor genes, which upon proper expression in the plant, are capable of inhibiting expression of a MS2 gene.

Inhibition of the expression of the MS2 gene will result in male-sterile plants. This can be accomplished by proper expression of an inhibitor gene directed against that target gene. Inhibitor genes can be suitably selected from a range of alternatives, including homologous or heterologous (i.e obtained from a different source) sense and antisense (synthetic)-genes or parts thereof with a suitable length and homology for proper inhibition, as illustrated in International Patent Application WO92/18625, MOGEN International NV and International Patent Application WO90/11682, DNA Plant Technology Inc.

Preferably the inhibitor gene is expressed in the tapetum according to the present invention. This can be accomplished by fusing the inhibitor gene under control of the promoter derived from the MS2 gene (see FIG. 4) from Arabidopsis or its heterologous counterpart (i.e obtained from another source).

Transfer of recombinant polynucleotides into plants or parts thereof can be achieved by numerous techniques. Some of them are listed here as illustration and comprise transformation of protoplasts using the calcium/polyethylene glycol method (Krens et al. 1982; Negrutiu et al., 1987), electroporation (Shillito et al., 1985), microinjection (Crossway et al., 1986), (DNA or RNA coated) particle bombardment (Klein et al., 1987), infection with viruses and the like, natural DNA transfer by Agrobacterium species preferably by the use of the so-called binary vector system (Bevan et al., 1984).

After identification of transformed plant material, whole plants are regenerated using well-known protocols described in literature (vide e.g. Horsch et al., 1985). There does not exist any restriction towards parts of the plants used.

After transformed plants have been obtained, they can be evaluated for the presence of the desired trait and/or the degree to which the desired traits are expressed. A first evaluation may include the level of expression of the inhibitor gene and the extent to which the transgenic plants are male-sterile. Subsequently transgenic plants can be selected that show stable and/or predictable inheritance of the male-sterile trait, and the like. Next the (heterozygous) male sterile plants can be used directly for the production of hybrid seed, or alternatively be selfed with rescued pollen in order for obtaining homozygous male-sterile plants. Clearly, the advantage of having a few homozygous male-sterile plants permits one to rapidly acquire large amounts of heterozygous male-sterile seed which can be directly used for large scale production of hybrid seed.

The present invention can be applied in any plant capable of self-pollination, for which the production of hybrid seeds is of commercial interest.

The invention also provides a method for obtaining homozygous male-sterile plants. This can be accomplished by selfing the heterozygous male-sterile plants according to the invention. The development of pollen of these plants can be rescued by overcoming the inhibition of in vivo MS2 protein synthesis. Inhibition of MS2 gene expression can be circumvented by allowing (temporary) in vivo production of MS2 protein in the tapetum of the plant. This can be achieved by introducing in addition to the inhibitor gene, a repair gene under control of an inducible promoter. In this configuration the expression of the repair gene can be externally controlled by adding an appropriate inducer. Preferably such a repair gene includes a gene at least containing part of the MS2 gene, that is capable upon expression of inhibiting the effect of expression of the antisense MS2 gene. Alternatively other approaches to inhibit the expression of an inhibitor gene as described in International Patent Application WO92/18625, MOGEN International N.V., can be used.

If hybrid crops are grown for their seed or fruit, inducible restoration of fertility is necessary. Male-sterility must then be eliminated to permit pollination and harvest of seed or fruit. Repairing male-fertility may be invoked by administration of an inducer to the crop in the field, causing a sufficiently high expression of the repair gene to neutralize the inhibition of the MS2 gene by the inhibitor gene.

ADVANTAGES

Former methods to provide nuclear male sterile plants involve expression of genes which encode products that are toxic to somatic cells, such as DNAses, RNAses, proteases or one of the enzymes involved in the chalcone biosynthesis pathway. Chalcone is a key compound in the flavonoid biosynthesis pathway. Flavonoids are secondary metabolites that are known to have a key-function in the pigmentation of flowers and fruit. In addition flavonoids appear to be involved in defense against phytopathogens (Lamb et al., 1989), the protection against UV-light (Schmelzer et al., 1988) and the induction of nodulation (Long, 1989). Flavonoids have also been implicated in the regulation of auxin transport (Jacobs and Rubery, 1988) and resistance to insects (Hedin and Waage, 1986). As a consequence of the properties mentioned above of the toxic products or the role of the product of the inhibited gene in the plant, strict developmental and tissue-specific expression limited to anthers only is required. The present method does not necessarily require such a strict developmental or tissue-specific expression.

Male-sterile plants according to the invention are highly sterile and appear entirely female-fertile.

The present invention also provides methods for obtaining homozygous male-sterile plants. Only a few are needed which can be multiplied in vitro by well-established techniques. The homozygous male-sterile acceptor plant is cross-fertilized with the male-fertile donor plant, and the heterozygous male-sterile seed used for hybrid crop production. Of the hybrid seed produced, 50% will be male-sterile and 50% male-fertile. In case this ratio is not sufficient for obtaining high yield of commercial product (i.e seed or fruit) by self-fertilization, this ratio can be ameliorated by partial restoration of male-sterility by administration of an inducer to activate expression of the restorer gene.

EXPERIMENTAL

Construction of plasmid cwEnN::I

The plasmid cwEnN::I used for *Agrobacterium tumefaciens* transformation was constructed with the aim of designing a phenotypic excision assay using kanamycin resistance, for the En-I transposon family, which can be used in a number of plant species. The binary vector pGDW3.1 (Wing et al., 1989) was the source of the chimeric nopaline synthase (nos) promoter-hygromycin phosphotransferase (HPT) gene used for selection during transformation. A chimeric neomycin phosphotransferase II (NPTII) gene was first inserted into pGDW3.1 which is similar to the NPTII gene used by Baker et al. (1987) except that a ClaI linker was introduced 5' to the unique BamHI present in the untranslated leader between the $T_R1'$ promoter and the NPTII codogenic region. This introduced a translation start (GCGATGG) 5' to the BamHI site. In addition, the NPTII translation start was removed by exchanging the NPTII gene sequences from plasmid pBCK1 (Kaulen et al., 1986) downstream of the BamHI site. This generated the plasmid pBHN in which a translation start is present upstream of the unique BamHI site into which an I element, I-6078 of 2.2 kb with 56 bp flanking DNA (Pereira and Saedler, 1989), was inserted to generate plasmid pBHNI.

En-1 (Pereira et al., 1986) was digested with BssHII, which cuts at positions 399 and 8041, made blunt with the Klenow fragment of DNA polymerase I and cloned between the cauliflower mosaic virus (CaMV) 35S promoter-terminator cassette, originating from pD51 (Pietrzak et al., 1986) in pBR322. This clipped-wing (cwEn) under control of the 35S promoter was next cloned into the binary vector pBHNI to produce plasmid cwEnN::I which was mobilized into the Agrobacterium strain pGV3101-(pMP90RK) (Koncz and Schell, 1986).

Plant transformation, propagation and phenotypic excision assay

For plant transformation, root explants of ecotype Landsberg erecta were infected with the Agrobacterium strain containing the binary vector construct, according to a method described by Valvekens et al. (1988). Transformed calli were selected on medium containing hygromycin at 20 mg.l$^{-1}$. Emerging $T_1$ shoots were grown without selection and allowed to self-fertilize and set seed in vitro. Seedset of *A. thaliana* is very poor in vitro due to high humidity. This was solved by lifting the lid of the pots a little. Growth conditions were 12 to 16 hrs light at 22° C. in growth chambers.

Seeds of $T_2$ and subsequent generations were sterilized in Eppendorf tubes by treatment with ethanol 70% (2 min), 50% commercial bleach (5% sodium hypochlorite, 5 min) and five subsequent washes with sterile water. The seeds were sown either wet or dry on GM medium (Valvekens et al., 1988) or half strength MS (Murashige and Skoog, 1962) solidified with 0.8% purified agar. For determining the number of T-DNA loci, seeds were mostly sown on half strength MS with 20 mg.l$^{-1}$ hygromycin. Using no sugar in the medium permitted sterilization with 70% ethanol for 2 min and only two to three washes with sterile water. Segregation of antibiotic resistance was scored 5 to 10 days after germination. If needed seedlings were transferred to soil (compost:vermiculite:sand=4:1:1) and grown in a climate controlled greenhouse at 20° C. with additional light (16 hrs). To prevent cross-fertilization and spread of seeds, plants were grown in Aracon containers (Beta Developments, Gent, Belgium). For the phenotypic excision assay seeds were germinated on GM medium containing 100 mg.l$^{-1}$ kanamycin sulphate. Resistance, variegation or sensitivity was scored 5 to 10 days after germination. Variegated and sensitive seedlings were transferred to GM without antibiotic to rescue them before transferring to soil.

Ploidy number was determined by counting chloroplasts in stomatal guard cells of the lower epidermis of young leaves as described by Detrez et al. (1989). At least 25 stomata of different $T_2$ and $T_3$ plants were regarded.

Genomic DNA isolation

Genomic DNA was isolated from young rosette leaves of individual greenhouse grown plants for both PCR and Southern analysis. The method we used was a modified version of the one described by Dellaporta et al. (1983). 100 mg of liquid $N_2$-frozen leaf tissue was grinded in a 1.5 ml Eppendorf tube and mixed with 300 µl of extraction buffer (100 mM Tris-HCl pH 8.0, 50 mM EDTA pH 8.0, 500 mM NaCl, 10 mM β-mercaptoethanol) and 25 µl of 20% SDS. The mix was incubated at 65° C. for 10 min, after which 115 µl 5 M potassium acetate was added, mixed and kept on ice for at least 20 min and then centrifuged. The DNA was precipitated from the resultant supernatant by adding 0.6 to 2 volumes of isopropanol and if needed kept at −20° C. for a few hours. The pellet was redissolved in 200 µl of TE (10 mM Tris-HCl pH 8.0, 1 mM EDTA pH 8.0) centrifuged for 5 min to remove debris, transferred to a new tube and RNase A added to 20 µg.ml$^{-1}$. The reaction mix was incubated at 37° C. for 15 min when Proteinase K was added upto 50 µg.ml$^{-1}$. After another 15 min at 37° C. the solution was phenol/chloroform extracted. DNA was precipitated again by adding 0.25 volumes of 10 M ammonium acetate and 2 volumes of 100% ethanol. The pellet was dissolved in 20 µl of TE. This procedure was either up or down scaled if different amounts of leaf tissue were used. It generally yielded about 1 to 2 µg of DNA per 100 mg leaf tissue.

DNA-methodology

DNA subcloning, restriction analyses and sequencing were performed using standard procedures well know to persons skilled in the art, vide e.g. Maniatis et al., 1982.

PCR and sequence analysis

Inverse PCR analysis to amplify transposon-flanking DNA of transformants was performed with 100 to 200 ng of genomic DNA. For the reaction 15 pmole of each primer was used, 0.1 mM of dNTPs (equal amounts of each dNTP) and 0.1 unit of SuperTaq DNA Polymerase (HT Biotechnology Ltd., Cambridge, England) in a total volume of 50 µl reaction buffer as supplied along with the enzyme (10 mM Tris-HCl pH 9.0, 50 mM KCl, 0.01% (w/v) gelatin, 1.5 mM MgCl$_2$ and 0.1% Triton X-100). 30 cycles of denaturation (94° C., 30 sec), annealing (61° C., 60 sec) and extension (72° C., 60 sec) were carried out. One tenth volume of PCR product was checked on agarose gel and if of interest cloned in Bluescript SK$^+$ as a blunt ended fragment after Klenow treatment and gel elution. Sequence analysis was performed on double stranded supercoiled plasmid using an automated sequencer (Applied Biosystems). Initially one strand, if needed both strands were sequenced.

Southern blot analysis

Genomic DNA was digested with both EcoRI and BglII and 0.5 to 1 µg was separated on a 0.8% agarose gel in Tris-acetate running buffer. After electrophoresis the DNA was alkali transferred onto a Gene Screen Plus membrane by vacuum blotting. The blots were prehybridized and hybridized following the procedure recommended by the membrane manufacturer. Probes (FIG. 1) were [$^{32}$P] random prime labelled DNA fragments. A 0.27 kb fragment containing the left border of En (upto a SalI restriction site) was used to detect I elements. The T-DNA right border probe was a 1.1 kb fragment containing the HPT gene. A fragment of 1.8 kb containing the complete NPTII gene plus octopine synthase (ocs) terminator was used to detect excision fragments. In the experiment shown in FIG. 5, MS2 cDNA was used as probe. After hybridization the membranes were washed twice with 2×SSC, 1% SDS at 65° C. for 30 minutes and autoradiographed to X-ray films (Fuji or Kodak) at −80° C. using intensifying screens.

Isolation of RNA

Plant material was collected, frozen in liquid $N_2$ and grinded using mortar and pestle. Equal volumes of extraction buffer (0.1 M Tris-HCl, pH 9.0, 1% SDS, 0.1 M LiCl, 0.01 M EDTA) and phenol were added (4 ml each) and the mixture incubated at 60° C. After centrifugation (10 min, 3000 rpm) the aquaous layer was extracted with 5 ml chloroform, collected and after addition of ⅓ volume of 8 M LiCl, RNA was allowed to precipitate overnight at 4° C. The RNA precipitate was collected by centrifugation at 4° C. (10 min, 12000 rpm) and washed twice with 70% ethanol. The dried pellet was finally dissolved in 0.06 M phosphate buffer pH 6.5.

Northern blotting

5 μl RNA (2 μg/ul) is denatured in 5 μl glyoxal and 10 μl DMSO for 60 min at 50° C. and separated according to length on a 1% agarose gel (3.5 h, 40 V) in 15 mM phosphatebuffer. Subsequently RNA is blotted to Hybond $N^+$ membrane according to the manufacturer (Amersham). The blot was prehybridized and hybridized following the procedure recommended by the membrane manufacturer. The probe (MS2 cDNA) was [$^{32}P$] random prime labelled. After hybridization the membranes were washed twice with 2×SSC, 1% SDS at 65° for 30 minutes and autoradiographed to X-ray films (Fuji or Kodak) at −80° C. using intensifying screens.

REFERENCES

Baker, B., Coupland, G., Fedoroff, N., Starlinger, P. and Schell, J. (1987) Phenotypic assay for excision of the maize controlling element Ac in tobacco. *EMBO J.* 6, 1547–1554.

Bevan, M. A. (1984) Binary Agrobacterium vectors for plant transformation. *Nucl Acids Res.* 12, 8711–8712.

Crossway, A., Oakes, J. V., Irvine, J. M., Ward, B., Knauf, V. C., Shewmaker, C. K. (1986) Integration of foreign DNA following microinjection of tobacco mesophyll protoplasts. *Mol. Gen. Genet.* 202, 179–185

Dellaporta, S. L., Woods, J. and Hicks, J. B. (1983) A plant DNA minipreparation version II. *Plant Mol. Biol. Rep.* 4, 19–21.

Detrez, C., Sangwan, R. S. and Sangwan-Norreel, B. S. (1989) Phenotypic and karyotypic status of *Beta vulgaris* plants regenerated from direct organogenesis in petiole culture. *Theor. Appl. Genet.* 77, 462–468.

Devereux, J., Haeberli, P. and Smithies, O. (1992) *Nucleic Acids Res.* 12, 387–395

Frey, M., Travantzis, S. M., and Saedler, H. (1989) *Mol. Gen. Genet.* 217, 172–177

Hedin, P. A. Waage, S. K. (1986) Roles of flavonoids in plant resistance to insects. In: *Progress in Clinical and Biological Research*. Vol. 213: Plant Flavonoids in Biology and Medicine. V. Cody, E. Middleton Jr., and J. B. Harborne, weds. (New York: Alan R. Liss), pp. 87–100.

Horsch, R. B., Fry, J. E., Hoffmann, N. L., Eichholtz, D., Rogers, S. G., Fraley, R. T. (1985) A simple and general method for tranferring genes into plants. *Science* 227, 1229–1231.

Jacobs, M., Rubery, P. H. (1988) Natural occuring auxin transport regulators. *Science* 241, 246–249.

Kaulen, H., Schell, J. and Kreuzaler, F. (1986). Light-induced expression of the chimeric chalcone synthase-NPTII gene in tobacco cells. *EMBO J.* 5, 1–8.

Klein, T. M., Wolf, E. D., Wu, R., Sanford, J. C. (1987) High-velocity microprojectiles for delivering nucleic acids into living cells. *Nature* 327, 70–73.

Koncz, C. and Schell, J. (1986). The promoter of $T_L$-DNA gene 5 controls the tissue-specific expression of chimaeric genes carried by a novel type of Agrobacterium binary vector. *Mol. Gen. Genet.* 204, 383–396.

Krens, F. A., Molendijk, L., Wullems, G. J., Schilperoort, R. A. (1982) In vitro transformation of plant protoplasts with Ti-plasmid DNA. *Nature* 296, 72–74

Lamb, C. J., Lawton, M. A., Dron, M., Dixon, R. A. (1989) Signals and transduction mechanisms for activation of plant defenses against microbial attack. *Cell* 56, 215–224.

Long, S. (1989) Rhizobium-legume nodulation: Life together in the underground. Cell 56, 203–214.

Masson, P. & Fedoroff, N. (1989) *Proc. Natn. Acad. Sci. U.S.A.* 86, 2219–2223

McClintock, B. (1954) *Carnegie Inst. Washington Year Book* 53, 254–260.

Negrutiu, I., Mouras, A., Horth, M., Jacobs, M. (1987) Direct gene transfer to plants: Present developments and some future prospectives. *Plant Physiol. Biochem.* 25, 493–503

Ochman, H., Gerber, A. S. & Hartl, D. L. (1988) *Genetics* 120, 621–623.

Maniatis, T., Fritsch, E. F., and Sambrook, J. (1982) *Molecular cloning: A Laboratory Manual* (Cold Spring Harbor, NY: Cold Spring Harbor Laboratory).

Murashige, T. and Skoog, F. (1962) A revised medium for rapid growth and bioassays with tobacco tissue cultures. *Physiol. Plant.* 15, 473–497.

Pereira, A., Cuypers, H., Gierl, A., Schwartz-Sommer, Zs. and Saedler, H. (1986). Molecular analysis of the En/Spm transposable element system of *Zea mays. EMBO J.* 5, 835–841.

Pereira, A. and Saedler, H. (1989). Transpositional behavior of the maize En/Spm element in transgenic tobacco. *EMBO J.* 8, 1315–1321.

Peterson, P. A. *Genetics* 38, 682–683 (1953).

Pietrzak, M., Shillito, R. D., Hohn, T. and Potrykus, I. (1986). Expression in plants of two bacterial antibiotic resistance genes after protoplast transformation with a new plant expression vector. *Nucl. Acids Res.* 14, 5857–5868.

Schwartz-Sommer, Zs., Gierl, A., Berndtgen, R. & Saedler, H. *EMBO J.* 4, 2439–2443 (1985).

Schmelzer, E., Jahnen, W., Hahlbrock, K. (1988) In situ localization of light-induced chalcone synthase mRNA, chalcone synthase and flavonoid endproducts in epidermal cells of parsley leaves. *Proc. Natl. Acad. Sci. USA* 85, 2989–2993.

Shillito, R. D., Saul, M. W., Paszkowski, J., Müller, M., Potrykus, I. (1985) High frequency direct gene transfer to plants. *Bio/Technology* 3, 1099–1103

Spencer, D. F., Schnare, M. N., Coulthart, M. B. and Gray, M. W. (1992) *Plant Mol. Biol.* 20, 347–352.

Valvekens, D., Van Montagu, M. and Van Lijsebettens, M. (1988). *Agrobacterium tumefaciens* mediated transformation of *Arabidopsis thaliana* root explants by using kanamycin selection. *Proc. Natl. Acad. Sci. USA.* 85, 5536–5540

Van den Elzen, P., Townsend, J., Lee, K. & Bedbrook, J. *Plant Mol. Biol.* 5, 299–302 (1985)

Van der Veen, J. H. & Wirtz, P. Euphytica 17, 371–377 (1968).

Weigel, D., Alvarez, J., Smyth, D. R., Yanofsky, M. F. & Meyerowitz, E. M. *Cell* 69, 843–859 (1992).

Wing, D., Koncz, C. and Schell, J. (1989). Conserved function in *Nicotiana tabacum* of a single Drosophila hsp70 promoter heat shock element when fused to a minimal T-DNA promoter. *Mol. Gen. Genet.* 219, 9–16.

We claim:

1. A recombinant polynucleotide for use in obtaining a male-sterile plant, comprising:
   a) a MS2 sense gene or a MS2 antisense gene capable of inhibiting the expression of a target gene, which target gene is present in the plant and encodes a protein indicated as MS2 which is involved in pollen development, said target gene having the nucleotide sequence of SEQ ID NO:1, or a nucleotide sequence coding for the same protein product as that encoded by SEQ ID NO:1, and
   b) a promoter that is active in the tapetum of said plant, operably linked to said MS2 sense gene or MS2 antisense gene as to achieve expression thereof in the tapetum of said plant.

2. A recombinant polynucleotide according to claim 1, wherein the promoter that is active in the tapetum of the plant comprises a MS2 promoter.

3. A method for obtaining a male-sterile plant, comprising the steps of
   a) transferring a recombinant polynucleotide according to claim 1 to cells of a male-fertile plant,
   b) generating whole new plants from cells having incorporated said recombinant polynucleotide and,
   c) selecting a plant that is male-sterile.

4. A recombinant plant genome comprising the recombinant polynucleotide of claim 1.

5. A male-sterile plant comprising the recombinant plant genome of claim 4.

6. A cell, fruit, seed or progeny each obtained from a male-sterile plant according to claim 5.

7. A seed of a male-sterile plant according to claim 5.

8. A homozygous male-sterile plant obtainable from a seed according to claim 7.

9. A cell, fruit, seed or progeny each obtained from plant of claim 8.

10. A method for the production of heterozygous male-sterile plants comprising fertilizing a homozygous male-sterile plant of claim 8 with a male-fertile plant, harvesting the seed and growing the heterozygous male-sterile plant from said seed.

11. A method for obtaining hybrid seed comprising the steps of crossing a male-sterile plant of claim 5 with a male-fertile plant and collecting the hybrid seed.

12. A method for obtaining hybrid seed comprising the steps of crossing a male-sterile plant of claim 8 with a male-fertile plant and collecting the hybrid seed.

13. The recombinant polynucleotide according to claim 2, wherein said MS2 promoter has the sequence of SEQ ID NO:3.

* * * * *